United States Patent [19]

Mononen et al.

[11] Patent Number: 5,106,376
[45] Date of Patent: Apr. 21, 1992

[54] ANAESTHESIA SET

[75] Inventors: Pekka Mononen, Savonlinna, Finland; Hans- G. Haindl, Melsungen; Peter Plantiko, Hanover, both of Fed. Rep. of Germany

[73] Assignee: B. Braun Melsungen AG, Melsungen, Fed. Rep. of Germany

[21] Appl. No.: 548,125

[22] Filed: Jul. 3, 1990

[30] Foreign Application Priority Data

Jul. 7, 1989 [DE] Fed. Rep. of Germany ...... 3922406

[51] Int. Cl.$^5$ ............................................. A61M 19/00
[52] U.S. Cl. ...................................... 604/164; 604/27; 604/43; 604/48; 604/49; 604/51; 604/158
[58] Field of Search ..................... 604/27, 28, 36, 38, 604/43, 158, 164, 165, 170, 181, 239, 264, 272, 48, 49, 51; 128/748, 760

[56] References Cited

U.S. PATENT DOCUMENTS

| 3,780,733 | 12/1973 | Manzor | 604/158 |
| 4,518,383 | 5/1985 | Evans | 604/164 |
| 4,685,904 | 8/1987 | Krebs | 604/164 |
| 4,737,146 | 4/1988 | Amaki et al. | 604/158 |
| 4,808,157 | 2/1989 | Coombs | 604/158 |
| 4,917,670 | 4/1990 | Hurley | 604/164 |
| 4,958,901 | 9/1990 | Coombs | 604/158 |

Primary Examiner—Stephen C. Pellegrino
Assistant Examiner—Glenn K. Dawson
Attorney, Agent, or Firm—Spensley Horn Jubas & Lubitz

[57] ABSTRACT

An anasesthesia set which includes a straight epidural cannula with a ground opening, a spinal cannula which is longer and thinner than the epidural cannula and which is insertable therein such that its front end projects from the epidural cannula, and a catheter adapted to be advanced through the epidural cannula. The tip of the epidural cannula is bent and the opening is directed sideward. A hole is formed in the outer wall of the bend of the tip. The hole is centered on the longitudinal central axis of the epidural cannula and is smaller than the outer diameter of an epidural catheter. The tip of the spinal cannula enters the spinal channel straightly, whereas the epidural catheter is deflected from the spinal channel and introduced into the epidural space. Without requiring any particular knowledge, spinal anaesthesia and epidural anaesthesia are performed in combination so that full use is made of the fast effect of the spinal anaesthesia and of the expansion of the area of the anaesthesia provided by the epidural analgesia. The duration of the analgesia is optionally extensible by subsequent injections.

7 Claims, 3 Drawing Sheets

ANAESTHESIA SET

BACKGROUND OF THE INVENTION

1. Field of the Invention

The present invention relates to an anaesthesia set, and in particular to an anaesthesia set comprising a straight epidural cannula with a ground opening, a spinal cannula which is longer and thinner than the epidural cannula and which can be inserted into the epidural cannula such that its front end projects from the epidural cannula, and a catheter adapted to be advanced through the epidural cannula.

2. Description of Related Art

When operating on the lower extremities and the organs in the pelvis, regional anaesthesia is substantially performed as spinal anaesthesia or epidural anaesthesia The advantages of spinal anaesthesia include: a quick effect, hardly any failures and a mostly complete analgesia. Among the drawbacks of spinal anaesthesia are that it is effective only approximately up to the hip, that the duration of the effect is limited with single shots, and that the introduction of a catheter into the spinal space can cause infections.

When performing spinal anaesthesia, a set of the above-mentioned type may be used (German Utility Model 88 11 408). In such a case, the cannula is a so-called Crawford cannula, the straight front tip of which is shortly bevelled and ground. The edges of the grinding are rounded in order to reduce the risk of a perforation of the dura. The thinner spinal cannula is advanced through the coaxial terminal opening of the epidural cannula to perforate the dura, and the catheter is advanced over a guide wire through the epidural cannula into the spinal space. An analgetic may be subsequently injected through the catheter (by means of a syringe, for example), at the extracorporeal end of which a connector is fixed.

In epidural anaesthesia. a catheter is introduced into the spinal space through an epidural cannula. This is less critical than it is in spinal anaesthesia. An optional duration of analgesia by subsequent injections and postoperative analgesia may be obtained. With the use of suitable analgetics, the analgesia may be maintained when the motorial function is restored. Although the effect occurs later than with spinal anaesthesia, epidural anaesthesia has an advantage over spinal anaesthesia in that it is effective up to the breast.

Thus, a combination of spinal and epidural anaesthesia, thereby combining the specific advantages of both techniques, could result in an extension of the region of the anaesthesia. However, the known sets for epidural anaesthesia do not allow a combination without risks. This is due to the fact that the dura is perforated by the advancement of the spinal cannula through the epidural cannula to inject an analgetic, and the epidural catheter (which is also advanced through the epidural cannula) contacts the dura at exactly the spot where it has previously been perforated. As a result, the epidural catheter will introduce the analgetic meant for the epidural space into the spinal space. This not only increases the anaesthetic risks to the patient, but also fails to spread the analgetic effect to that part of the body intended to be anaesthetized by the epidural anaesthesia.

It is an object of the present invention to provide an anaesthesia set of the type mentioned above such that it allows a simple and riskless use in combined spinal and epidural anaesthesia.

SUMMARY OF THE INVENTION

In accordance with the present invention. this and other objectives are achieved by providing an epidural cannula having a bent tip and an opening which is directed sideward A hole for letting through the spinal cannula is arranged in the epidural cannula. The hole is centered on the longitudinal central axis of the epidural cannula in the outer wall of the bend of the tip. The hole is smaller than the outer diameter of an epidural cannula.

In the anaesthesia set of the present invention, first, the epidural cannula (the lumen of which may be filled with a stylet in order to prevent punching), may be advanced through the muscle tissue into the epidural space up to the outer wall of the dura. Thereafter, the stylet may be removed and a thinner and longer spinal cannula with a stylet may be introduced into the epidural cannula. The spinal cannula emerges from the coaxial hole in the bend of the epidural cannula and perforates the dura. After the withdrawal of the stylet from the spinal cannula, an analgetic may be injected into the spinal space. The spinal cannula may be withdrawn from the epidural cannula and an epidural catheter may be advanced through the epidural cannula. The epidural catheter, which does not fit through the sideward, following the bend of the tip of the epidural cannula and—depending on the orientation of the lateral opening of the epidural cannula—may be advanced upward or downward in parallel to the dura.

Since the epidural catheter cannot meet the perforation in the dura, the risk of an unintentional intrathecal position of the catheter is practically excluded. Handling the set of three elements is simple for a user, because the tip of the spinal cannula inevitably enters the spinal channel straightly, whereas the epidural catheter is inevitably deflected from the spinal channel and introduced into the epidural space. Without requiring any particular knowledge, spinal anaesthesia and epidural catheter anesthesia are performed in combination so that full use may be made of the fast effect of the spinal anaesthesia and of the expansion of the area of the anaesthesia provided by the epidural analgesia, the duration of the analgesia being optionally extensible by subsequent injections.

In order to provide an easy non-jamming passage of the spinal cannula, the hole in the tip of the epidural cannula may preferably be oval and the longitudinal axis of the hole may preferably extend in parallel to the longitudinal axis of the epidural cannula. The hole may be burnt into the steel walls of the epidural cannula by means of a laser beam.

A coaxial guide ring may be fastened to the spinal cannula, preferably at a distance from the tip thereof, the outer diameter of the ring being slightly smaller than the inner diameter of the epidural cannula. The coaxial guide ring, which may be of metal or plastic material, serves to center the tip of the overlong spinal cannula in the center of the epidural cannula so that it may be guided to issue from the coaxial hole of the epidural cannula. Such guiding is advantageous, since the spinal cannula may be extremely thin and unstable, so that its tip tends to divert and to miss the coaxial hole when being advanced through the epidural cannula with a larger inner diameter The guide ring may be provided as a circumferentially closed circularly cylindrical tube enclosing the spinal cannula from the cannula hub up to the region of the tip. The end of the spinal cannula projecting beyond the epidural cannula is free of the guide ring. Instead of a long tube, one may also use a short tube portion as the guide ring, which is provided only in the region close to the tip of the spinal cannula.

BRIEF DESCRIPTION OF THE DRAWINGS

A detailed description of a preferred embodiment of the invention will be made with reference to the accompanying drawings.

FIG. 3A is an up-scaled illustration of a portion of an anaesthesia set adjacent the tip in the stages of FIGS. 3 and 4.

DETAILED DESCRIPTION OF PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

Figure 1:
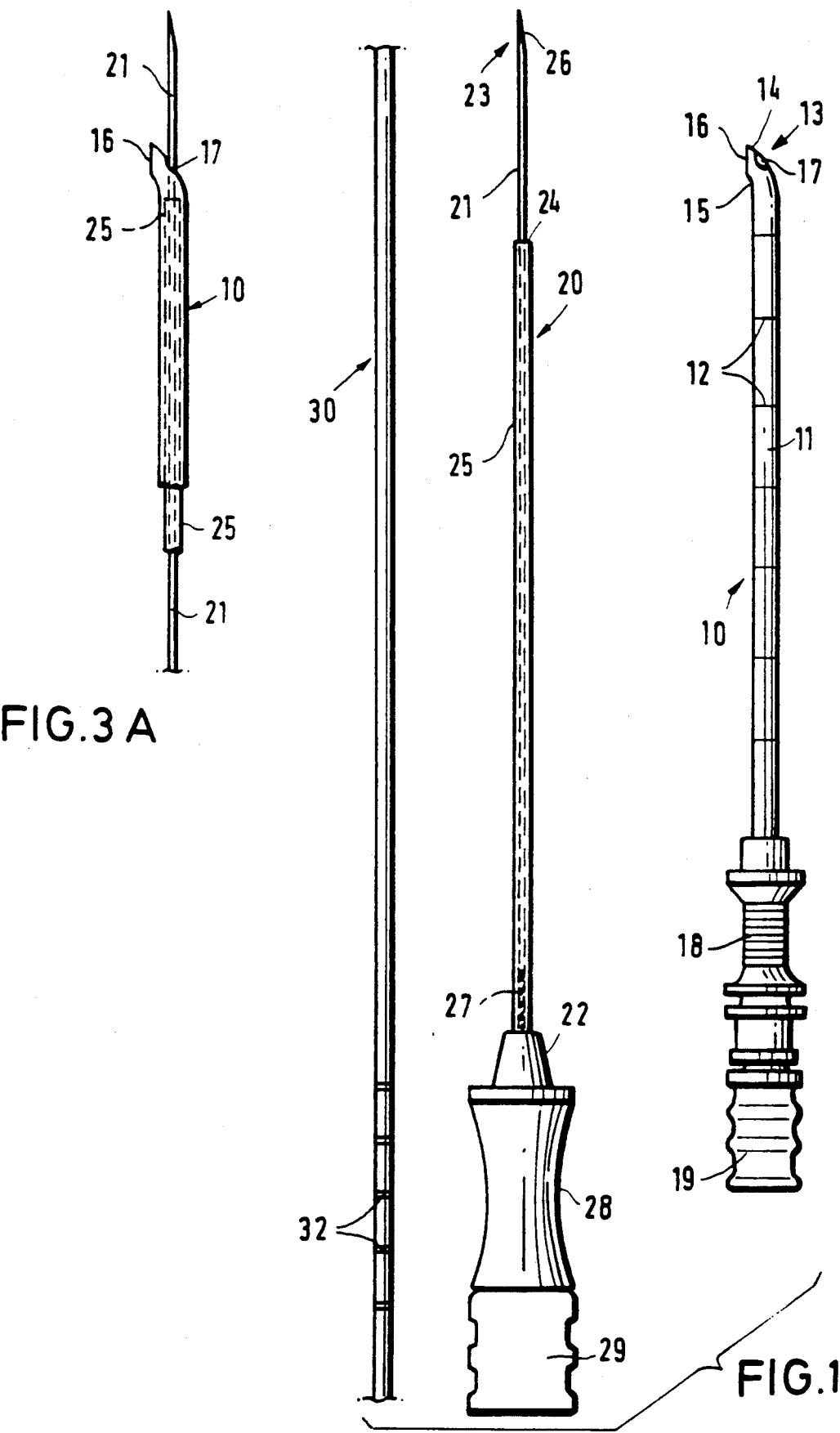
FIG. 1 shows an illustration of the components of an anaesthesia set.

As illustrated in FIG. 1, an epidural cannula 10 is provided that consists of a straight cannula tube 11 of steel having marker rings 12 for controlling the length of insertion. The tip 13 of the epidural cannula 10 is bent towards one side, so that a bend defining an outer wall 14 and an inner wall 15 is formed and the terminal opening 16 is directed sideward The opening 16 extends substantially parallel to the cylindrical wall of the cannula tube 11 and has a grinding suited for puncturing tissue.

The epidural cannula 10 may be a Touhy-type cannula in which a stylet, preferably of plastic, is situated. The stylet is represented in FIG. 1 by its handle piece 19 which sits in a cannula hub 18 of the cannula tube 11. The tip of the stylet has a bevelling which is flush with the opening 16 when the stylet is in the predetermined alignment in the cannula tube 11.

The outer wall 14 of the bend of the tip 13 of the cannula tube 11 may be provided with an oval hole 17. The longitudinal axis of the hole 17 may extend parallel to the longitudinal axis of the cannula tube 11, and the center of the hole 17 may be centered on the longitudinal central axis of the cannula tube 11.

The spinal cannula 20 may be longer and much more delicate than the epidural cannula 10. It consists of a thin cannula tube 21. The tip 23 of the cannula tube 21 has an oblique opening 26 with a sharp grinding which may be a Quincke-grinding in order to obtain a minimum area of puncture The end of the cannula tube 21 far from the tip 23 has a cannula hub 28 attached thereon which has an outer cone 22 at the end facing the cannula and an inner connecting element at the other end for applying a syringe. The outer cone 22 serves as a plug connection with an inner cone of the cannula hub 18 of the epidural cannula 10 The lumen of the spinal cannula 20 may be filled with a metal stylet 27 as fine as a hair, which can be withdrawn from the spinal cannula by means of a handle piece 29.

Over most of its length, the cannula tube 21 may be enclosed by a circularly cylindrical plastic tube 25. The plastic tube 25 may be attached at the outer cone 22 of the cannula hub 28 and may tightly enclose the cannula tube 21 by being shrunk thereon so that the cannula tube may be stabilized in the plastic tube 25. The uniform outer diameter of the plastic tube 25 may be slightly smaller than the inner diameter of the cannula tube 11 of the epidural cannula 10. The length of the plastic tube 25 may be adapted to the length of the cannula tube 11 up to the beginning of the bend. When the spinal cannula 20 is advanced through the epidural cannula 10 and when its tip 23 passes through the hole 17 in the epidural cannula 10 in a centered manner, the portion of the spinal cannula 20 protruding beyond the straight dull edge 24 of the plastic tube 25 may project from the hole 17 of the epidural cannula 10, due to the tip being guided by the plastic tube 25.

Another component of the anaesthesia set may be an epidural catheter 30. This catheter may consist of an elongate flexible catheter hose, the outer diameter of which approximates the outer diameter of the plastic tube 25 on the spinal cannula 20; i.e., the outer diameter of the catheter 30 may be somewhat smaller than the inner diameter of the epidural cannula 10. The tip of the epidural catheter 30 has a terminal coaxial opening with rounded edges. The opposite end has a connector (not illustrated) for connecting a syringe or the like. Further, the rear end of the catheter hose may be provided with markers 32 for checking the length of insertion.

The application of the anaesthesia set of FIG. 1 is illustrated in FIGS. 2 to 6.

Figure 2:
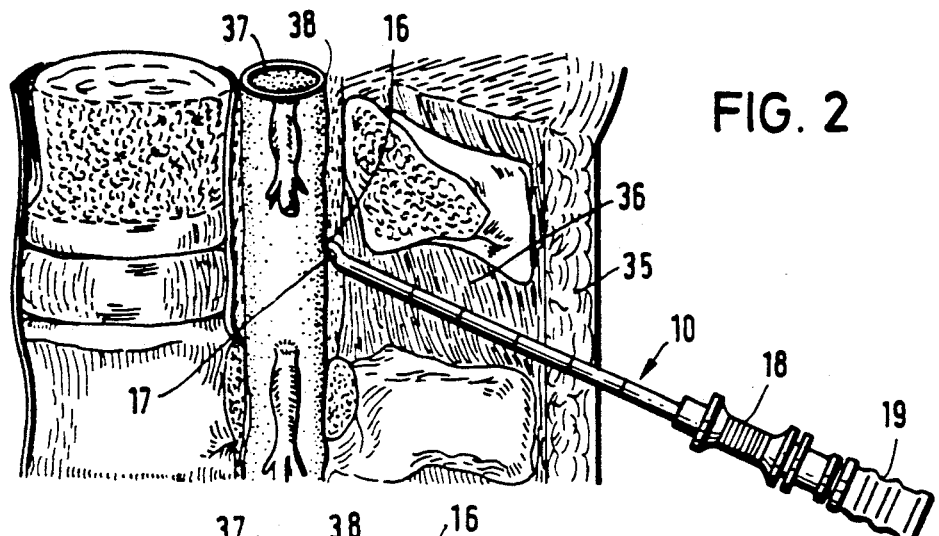
FIGS. 2 to 6 show the different stages of an application of a catheter set.

First, the skin 35 and the muscle tissue 36 are perforated by the epidural cannula 10 filled with the stylet, until the outer wall 14 of the tip 13 of the epidural cannula 10 abuts the outside of the dura 38 enclosing the spinal channel 37. In doing so, the opening 16 of the epidural cannula 10 may be advantageously directed upward and the hole 17 points to the dura 38 (FIG. 2).

Figure 3:
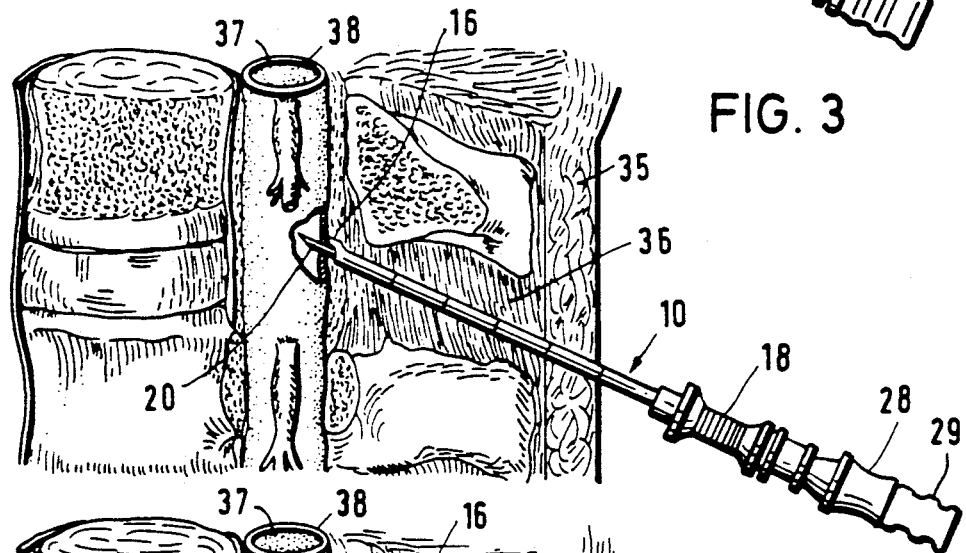

After the withdrawal of the stylet from the epidural cannula lo, the spinal cannula 20 with the stylet 27 located therein may be inserted into the epidural cannula 10 up to the intrathecal space. In doing so, the spinal cannula 20 may be centered by the plastic tube 25 in the center of the epidural cannula 10 so that the tip 26 of the spinal cannula 20 will issue from the hole 17 and perforate the dura 38 (FIG. 3).

Figure 4:
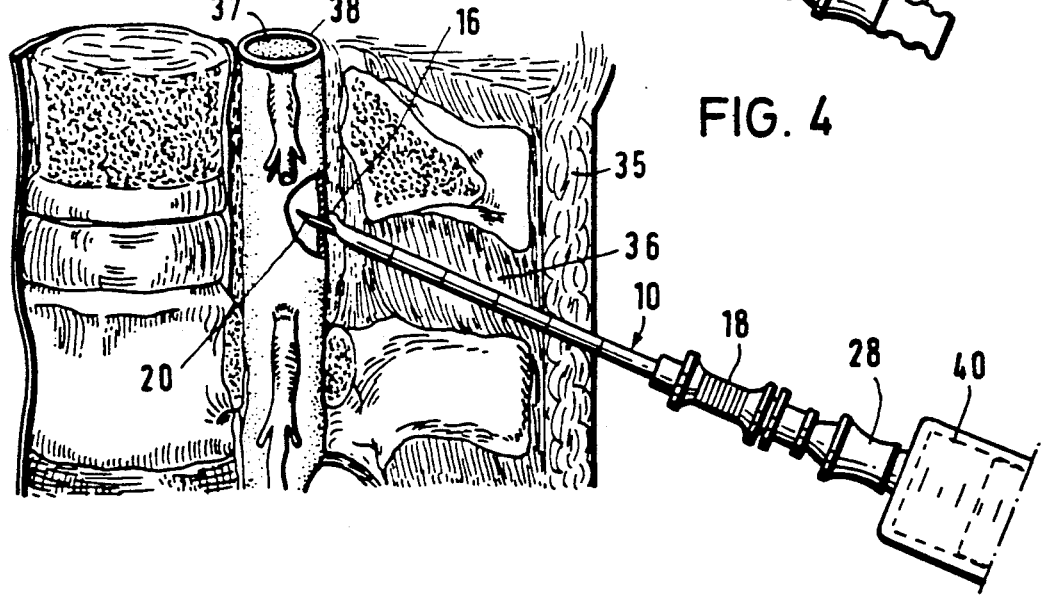

When the tip 26 of the spinal cannula 20 has reached the spinal channel 37, the stylet 27 may be withdrawn from the spinal cannula 20, and the connecting element of the cannula hub 28 may be coupled with a fitting hub of syringe 40 from which an analgetic for spinal anaesthesia may be injected into the spinal space 37 (FIG. 4).

Figure 5:
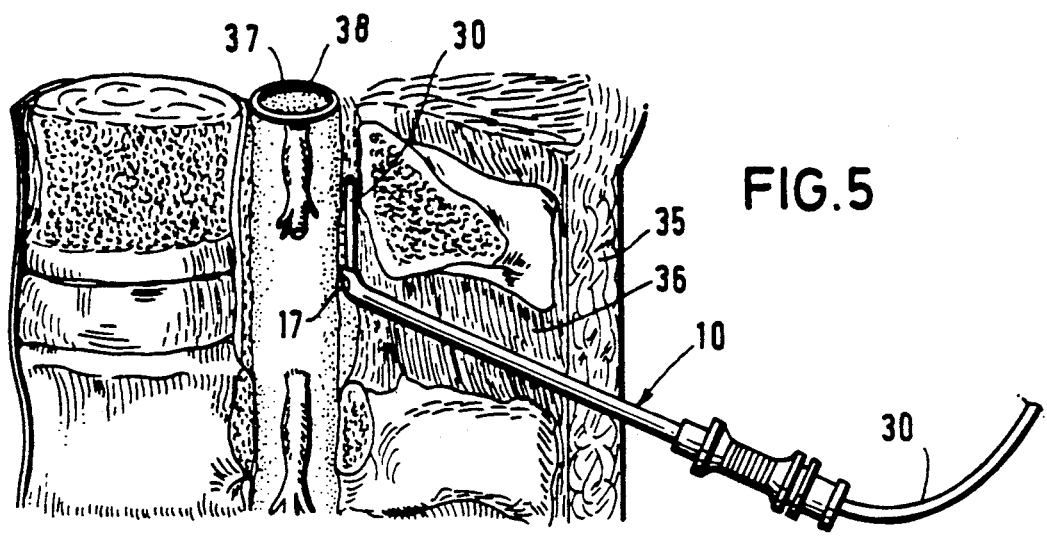
Figure 6:
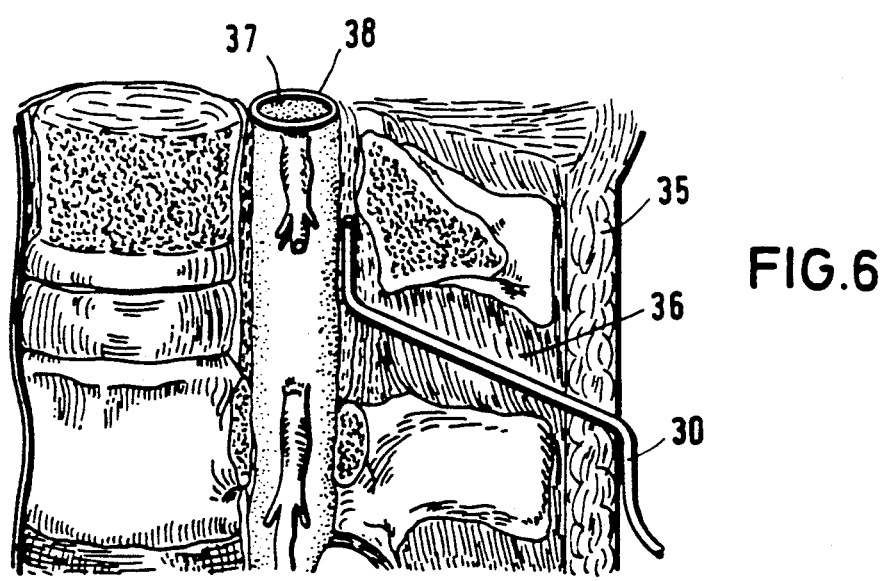

After the spinal cannula 20 has been withdrawn from the epidural cannula 10, the epidural cannula 10 may be used as a guide means for the epidural catheter 30 (FIG. 5). The epidural catheter 30 may be advanced through the cannula hub 18 and the cannula tube 11 until it hits the bend at the tip of the epidural cannula 10. Since the epidural catheter 30 does not fit through the axial hole 17, the epidural catheter is deflected sideward following the bend of the cannula and will glide upward along the dura 38. The penetration of the epidural catheter 30 into the spinal space 37 may be positively prevented and the risk of an unintentional intrathecal position of the catheter may be virtually excluded. Subsequently, the epidural cannula 10 may be axially pulled from the epidural catheter 30 so that the situation shown in FIG. 6 will occur.

Finally, a connector (not illustrated) may be connected to the rear catheter end to inject analgetics into the epidural space in front of the dura 38 through a syringe applied to the connector. Thus, one may obtain an optional duration of the analgesia by subsequent injections. The epidural anaesthesia is also well suited for postoperative analgesia.

The presently disclosed embodiment is to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An anaesthesia set comprising:
    an epidural cannula defining a leading end, a first aperture, and a substantially longitudinal central axis,
    a spinal cannula defining a front end and being adapted for insertion into the epidural cannula, the spinal cannula and the epidural cannula being mutually configured so that the front end of the spinal cannula projects beyond the leading end of the epidural cannula when the spinal cannula is inserted into the epidural cannula, and
    an epidural catheter defining an outer diameter and being adapted for insertion into the epidural cannula,
    the epidural cannula further defining a bent tip having an outer wall and a second aperture formed in the outer wall of the bent tip, the second aperture being coaxial with the longitudinal central axis of the epidural cannula and having a diameter which is smaller than the outer diameter of the epidural catheter, whereby the second aperture serves as a passage for the spinal cannula.

2. The anaesthesia set of claim 1, wherein the second aperture is substantially oval in shape and wherein the second aperture defines a longitudinal axis extending substantially coaxial with the longitudinal central axis of the epidural cannula.

3. An anaesthesia set comprising:
    an epidural cannula defining a leasing end, a first aperture, and a substantially longitudinal central axis,
    a spinal cannula defining a front end and being adapted for insertion into the epidural cannula, the spinal cannula and the epidural cannula being mutually configured so that the front end of the spinal cannula projects beyond the leading end of the epidural cannula when the spinal cannula is inserted into the epidural cannula, and
    an epidural catheter defining an outer diameter and being adapted for insertion into the epidural cannula,
    the epidural cannula further defining a bent tip having an outer wall and a second aperture formed in the outer wall of the bet tip, the second aperture being coaxial with the longitudinal central axis of the epidural cannula and having a diameter which is smaller than the outer diameter of the epidural catheter, wherein the epidural cannula defines an inner diameter and further comprising a coaxial guide ring mounted on the spinal cannula, the guide ring defining an outer diameter which is smaller than the inner diameter of the epidural cannula.

4. The anaesthesia set of claim 3, wherein the guide ring comprises a circumferentially closed circularly cylindrical tube.

5. The anaesthesia set of claim 4, wherein the tube comprises a hose of plastic material substantially enclosing the spinal cannula and exposing a section of the spinal cannula adjacent the front end.

6. An anaesthesia set for delivering anesthetic to a spinal channel and an epidural space, comprising:
    an epidural cannula having a substantially longitudinal central axis,
    a spinal cannula adapted for advancement through the epidural cannula,
    an epidural catheter adapted for advancement through the epidural cannula,
    the epidural cannula defining a bent tip having an outer wall, a first aperture and a second aperture, the second aperture being formed in the outer wall of the bent tip and being substantially coaxial with the longitudinal axis of the epidural cannula,
    the epidural cannula and the spinal cannula being mutually configured to enable the spinal cannula to be advanced through the second aperture,
    the epidural cannula and the epidural catheter being mutually configured to prevent the epidural catheter from being advanced through the second aperture and to enable the epidural catheter to be advanced through the first aperture,
    whereby the spinal cannula is advanced through the epidural cannula and the second aperture toward the spinal channel and whereby the epidural catheter is advanced through the epidural cannula and the first aperture toward the epidural space, whereby the second aperture serves as a passage for the spinal cannula.

7. An method of delivering anesthetic to a spinal channel and an epidural space, comprising:
    providing an epidural cannula having a substantially longitudinal central axis, the epidural cannula defining a bent tip having an outer wall, a first aperture and a second aperture, the second aperture being formed in the outer wall of the bent tip and being substantially coaxial with the longitudinal axis of the epidural cannula,
    advancing the epidural cannula through skin and muscle tissue to the outside of the dura enclosing the spinal channel,
    advancing a spinal cannula through the epidural cannula and the second aperture into the spinal channel,
    delivering an analgetic through the spinal cannula into the spinal channel,
    withdrawing the spinal cannula from the epidural cannula,
    advancing an epidural catheter through the epidural cannula and the first aperture into the epidural space,
    withdrawing the epidural cannula over the epidural catheter, and
    administering anaesthesia through the epidural catheter to the epidural space.

* * * * *